United States Patent [19]

Kelly

[11] Patent Number: 4,602,100

[45] Date of Patent: Jul. 22, 1986

[54] ORGANO METALLIC COMPLEXES AND THE USE THEREOF IN EPOXIDATION OF OLEFINS

[75] Inventor: Raymond L. Kelly, Swanland, England

[73] Assignee: BP Chemicals Limited, London, England

[21] Appl. No.: 661,355

[22] Filed: Oct. 16, 1984

[30] Foreign Application Priority Data

Oct. 18, 1983 [GB] United Kingdom ................ 8327810

[51] Int. Cl.$^4$ .................... C07D 303/04; C07D 301/06
[52] U.S. Cl. .................................. 549/529; 525/328.2
[58] Field of Search ...................... 525/328.2; 549/529

[56] References Cited

U.S. PATENT DOCUMENTS

| | | | |
|---|---|---|---|
| 2,888,441 | 5/1959 | Morris | 525/328.2 |
| 3,489,775 | 1/1970 | de Roch | 549/529 |
| 3,505,360 | 4/1970 | Allison | 549/529 |
| 3,887,361 | 6/1975 | Lemke | 549/529 |
| 3,985,540 | 10/1976 | Fein | 525/328.2 |

FOREIGN PATENT DOCUMENTS

| | | | |
|---|---|---|---|
| 0124231 | 11/1984 | European Pat. Off. | 549/529 |
| 2446216 | 4/1976 | Fed. Rep. of Germany | 549/529 |
| 1173494 | 12/1969 | United Kingdom | 549/529 |
| 285236 | 10/1970 | U.S.S.R. | 525/328.2 |

OTHER PUBLICATIONS

Topich, "Ligand Control of the Redox Properties of Dioxomolybdenum (VI) Coordination Complexes", Inorganic Chem., 1981, vol. 20, pp. 3704–3707.

*Primary Examiner*—C. Warren Ivy
*Attorney, Agent, or Firm*—Brooks Haidt Haffner & Delahunty

[57] ABSTRACT

A family of polymer bound organometallic complexes comprises compounds derived from a metal and a functionalized organic polymer of formula

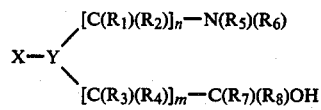

wherein X is a polymer backbone bonded to a ligand in which; Y is a group derived from an atom selected from C, Si, N and P; $R_1$, $R_2$, $R_3$ and $R_4$ are, independently, groups selected from H, a $C_1$–$C_4$ alkyl group and a halogen atom; $R_5$ and $R_6$ are, independently, groups selected from H, a $C_1$–$C_4$ alkyl group and a halogen atom, or together with the nitrogen atom form a heterocyclic ring having 5 or 6 atoms; $R_7$ and $R_8$ are, independently, groups selected from H, a $C_1$–$C_4$ alkyl group, an aryl group and a halogen atom and each of n and m have a value from 0 to 10. When the metal is either molybdenum or vanadium the complexes are suitable catalysts for the epoxidation of olefins.

12 Claims, No Drawings

ORGANO METALLIC COMPLEXES AND THE USE THEREOF IN EPOXIDATION OF OLEFINS

The present invention relates to novel organometallic complexes and the use thereof as catalysts, especially for the epoxidation of olefinic compounds.

It has been reported by Bhaduri, S. et al in the Journal of Chemical Society (Dalton) Transactions, 1983, pp 415 that polymer supported complexes of molybdenum thiocarbamate derivatives can be used as catalysts in epoxidation reactions. The catalyst is said to require an olefin to peroxide ratio, eg cyclohexene to tert-butyl hydroperoxide ratio of at least 25:1 in order to achieve a yield of 70%. The reported epoxidation reaction also takes a relatively long time (18 hours). The reference also states that for the oxidation of dimethyl sulphoxide the activity of the catalyst diminished by a factor of three after four runs of five hours. The only olefin epoxidised by Bhaduri et al is cyclohexene.

It has now been found that by a suitable choice of an organic ligand which is bound to a polymer, an improved epoxidation catalyst may be produced.

Accordingly, the present invention provides polymer bound organometallic complexes derived from a metal and a functionalised organic polymer of the formula

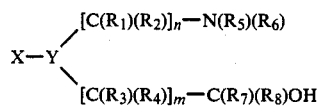

wherein X is a polymer backbone bonded to a ligand in which

Y is a group derived from an atom selected from C, Si, N and P, $R_1$, $R_2$, $R_3$ and $R_4$ are, independently, groups selected from H, a $C_1$-$C_4$ alkyl group and a halogen atom, $R_5$ and $R_6$ are, independently, groups selected from H, a $C_1$-$C_4$ alkyl group and a halogen atom, or together with the nitrogen atom form part of a heterocyclic ring containing 5 or 6 atoms, $R_7$ and $R_8$ are, independently, groups selected from H, a $C_1$-$C_4$ alkyl group, an aryl group and a halogen atom, and each of n and m have a value from 0 to 10 such that the polymer X is bound to the ligand through Y and the metal is complexed with the functionalised organic compound through the nitrogen atom in the $N(R_5)(R_6)$ group and the oxygen atom in $C(R_7)(R_8)OH$ group.

In the organometallic complex the polymer X may be any polymer capable of providing a backbone for the primary ligand and which has the ability to form a stable bond with the primary ligand. Any polymer would be suitable provided that (a) it does not adversely affect the reactivity of the catalyst, (b) the bond formed with the primary ligand is stronger than that between the metal and the primary ligand, and (c) it is chemically stable under the reaction conditions.

Examples of the polymer that may be used include polystyrene, polyamides and polyolefins. Polystyrene is the preferred polymer.

The group Y in the ligand is derived from an atom selected from C, Si, N and P. Thus, when the group Y is derived from C and Si, it may be a group selected from —$CR_9$ and —$SiR_9$ in which $R_9$ represents H, a $C_1$-$C_4$ alkyl, an aryl or an —OH group.

The other group and substituents in the primary ligand namely $R_1$-$R_4$, $R_7$ and $R_8$ are suitably selected from H or a $C_1$-$C_4$ alkyl group. The groups $R_5$ and $R_6$ are suitably such that they, together with the nitrogen atom, form a six-membered heterocyclic ring.

The number of $C(R_1)(R_2)$ and $C(R_3)(R_4)$ groups in the ligand are represented by the integers n and m respectively. The integers n and m, which may be identical or different, suitably have a value from 1 to 6, preferably from 1 to 3. A specific example of the organic compound from which such a primary ligand may be derived is N-(2-hydroxypropyl)-2-picolylamine in which the ligand is attached to the polymer, eg polystyrene, backbone through the nitrogen atom of the picolyl amine.

The compound may be graphically represented as

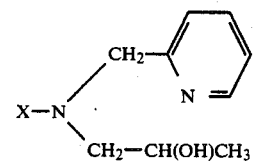

wherein X is polystyrene. Such a product is available as a proprietary compound from the Dow Chemical Company.

Other compounds from which the ligands may be derived include 8-hydroxyquinoline, ethylene bis(salicylimine), phenylene bis(salicylimide), salicylaldoxime and 2-pyridylcarbinol.

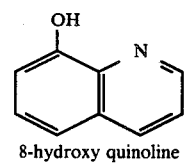

8-hydroxy quinoline

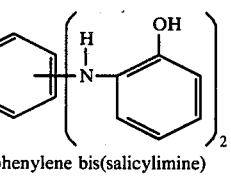

phenylene bis(salicylimine)

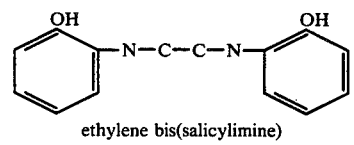

ethylene bis(salicylimine)

salicylaldoxime

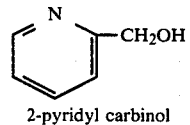

2-pyridyl carbinol

The metal atom in the organometallic complex is suitably molybdenum or vanadium.

The complexes may be derived by reacting a suitable functionalised organic compound with a metal complex eg a molybdenum or vanadium complex containing secondary ligands which are readily displaced by the ligands referred to above.

Examples of metal complexes used to produce the novel organo metallic complexes include molybdenum acetyl acetonate, the hydroxyethylene glycollate of molybdenum and the like.

The novel organometallic complexes of the present invention are useful as catalysts, especially for epoxidising olefins.

Specific examples of the olefins that may be epoxidised using the complexes of the present invention as catalysts include ethylene, propylene, butylenes, pentenes, hexenes, cyclohexene, styrene and the like.

The epoxidation reaction is suitably carried out in the heterogeneous liquid phase, the catalyst being in the solid phase.

The epoxidation is carried out using any of the conventional hydroperoxides as the oxidising agent. It is preferable to use alkyl or aryl hydroperoxide for example tert-butyl hydroperoxide and cumyl, hydroperoxide.

Examples of solvents that may be used as the reaction medium for the liquid phase epoxidation are hydrocarbons such as benzene, cyclohexane and cyclohexene; halogenated hydrocarbons such as dichlorobenzene; and alcohols such as tertiary butanol.

Thus, the olefin, the polymer bound organometallic complex and the hydroperoxide may be contacted in an oxidant-stable organic solvent and placed in a reaction vessel equipped with a stirrer and thermometer. The molar ratio of the organometallic complex to the hydroperoxide is suitably between 0.005:1 and 0.1:1, preferably between 0.002:1 and 0.05:1.

Alternatively, the reaction may be carried out by passing a mixture of olefin, hydroperoxide and solvent through a bed of the catalyst.

An excess of the solvent may be used in relation to the hydroperoxide. For instance, between 1.2 and 50 volumes of the solvent may be used per volume of the hydroperoxide.

The epoxidation reaction occurs in the presence of an excess of the olefins in relation to the hydroperoxide so as to maximise the utilisation of the latter. The olefin to hydroperoxide molar ratio is suitably from 0.5:1 to 100:1, preferably from 2:1 to 20:1.

As regards the temperature of the reaction, this is suitably in excess of 50° C. and is preferably in the range 50°–150° C.

A surprising feature of the present invention is the ability of the catalyst to epoxidise the relatively inert olefin ethylene in the presence of an autocatalytic agent such as cyclohexene oxide. Thus if the mixture of the organometallic complex and the hydroperoxide is added to a mixture of ethylene with cyclohexene oxide, the conversion and selectivity to ethylene oxide is surprisingly improved. The product epoxide, ie ethylene oxide may be used as the autocatalytic agent instead of cyclohexene oxide. The amount of epoxide added to the reaction mixture will depend upon the olefin being epoxidised. In general it is suitably between 1 and 10 moles per mole of the catalyst.

Yet another feature of the complexes of the present invention is that they retain their activity for epoxidation, especially for cyclohexene, for long periods of time without showing a fall off in activity.

The preparation of the polymer bound organometallic complexes of the present invention and the use thereof as catalysts is further illustrated by the following Examples.

EXAMPLE 1

Catalyst Preparation

N-(2-hydroxypropyl)-2-picolyl amine bound on a polystyrene backbone (bought from the Dow Chemical Company as Dowex XFS-43084) as received was washed well with methanol and dried overnight in an oven at 60° C. 5 g of this resin was refluxed for 6 hours together with 5 g of $MoO_2(OCH_2CH_2OH)_2$ in a mixture of 50 ml tetrahydrofuran and 50 ml ethanol. The resulting blue-green beads were filtered off, washed well with methanol and dried overnight at 60° C. The yield of catalyst was 6.58 g, and the molybdenum content of beads was 18.7% w/w.

EXAMPLE 2

Propylene Epoxidation

An autoclave was charged with 20 ml of a 3.28 molar solution of tert-butyl hydroperoxide in toluene (0.066 moles tert-butyl hydroperoxide):1 g of the above catalyst and 36 mls (18.7 g, 0.44 moles) of propylene. The reaction mixture was heated to 90° C. for 2 hours after which it was analysed. The overall yield of propylene oxide was 57.4% with 73.3% tert-butyl hydroperoxide converted corresponding to a selectivity to propylene oxide based on tert-butyl hydroperoxide converted of 78.3%. The selectivity to propylene oxide based on propylene was virtually quantitative.

The catalyst was isolated at the end of the run, washed with toluene, dried overnight at 60° C. and reused for the next run. This procedure was repeated for 6 successive runs and the results showed that the catalyst activity was retained throughout the six runs.

EXAMPLE 3

Cyclohexene Epoxidation

Continuous epoxidation of cyclohexene was carried out in the following manner. 3.3 g of the catalyst was packed into a U-tube reactor and a mixture of 100 ml 3.3 molar tert-butyl hydroperoxide in toluene, 100 ml cyclohexene and 2.53 g undecane (internal GC standard) pumped through at a rate of 40 ml per hour (6 minute residence time). The reactor was maintained at 90° C. Initial conversions of tert-butyl hydroperoxide of 70–75% with 90–100% selectivity to cyclohexene oxide were maintained over the 150 hour trial.

COMPARATIVE TEST A

This comparison test, taken from J. Chem. Soc. (Dalton Trans) p418 (1983) illustrates that the catalysts of the prior art are inferior to those disclosed in the present document.

Beads of cross-linked polystyrene supported [$Mo_2O_3(S_2CWEt_2)_4$] (1.0 g, 0.72 mmol of molybdenum), cyclohexene (5 cm$^3$, 50 mmol), benzene (20 cm$^3$) and tert-butylhydroperoxide (0.13 cm$^3$, 1 mmol) were stirred together for 24 hours at room temperature. The e.s.r. spectrum of a portion of the beads isolated after 12 hours showed only a weak signal identical to that of the functionalised cross-linked polystyrene. GC analysis after 12 hours and 24 hours showed a total absence of cyclohexene oxide. The beads were filtered off after 24 hours, washed with benzene, and treated with cyclohexene (2.5 cm$^3$, 25 mmol) and t-butyl hydroperoxide (0.13 cm$^3$, 1 mmol) and benzene (20 cm$^3$) at 60° C. for 18 hours. GC analysis at the end of this period showed the presence of cyclohexene oxide (0.073 g, 0.75 mmols).

The above test shows that the catalysts of the prior art are inferior to those claimed in the present document. Thus in the prior art, long residence times (18 hours) were required to secure reasonable conversion compared to the 6 minutes used in Example 3.

EXAMPLE 4

Ethylene Epoxidation

A 100 ml autoclave was charged with 20 ml of 4.87 molar tert-butyl hydroperoxide solution in toluene and 2.5 g of the catalyst. 50 bar ethylene pressure was applied, the autoclave sealed and heated to 90° C. for 3 hours with stirring. The autoclave was cooled and the contents analysed by gas chromatography. The conversion of tert-butyl hydroperoxide was 42.3%, with 20.6% selectivity to ethylene oxide. The catalyst was washed with toluene, dried and reused for successive runs over which its performance improved. After 6 runs, the conversion of tert-butyl hydroperoxide was 59.5% with 40.8% selectivity to ethylene oxide.

I claim:

1. A process for the epoxidation of an olefin which process comprises reacting an olefin with a hydroperoxide in an oxidation stable organic solvent at a temperature in excess of 50° C., characterised in that the reaction is carried out in the presence of, as catalyst, an effective amount of a polymer bound organometallic complex comprising a metal selected from molybdenum and vanadium, and a functionalised organic polymer of the formula

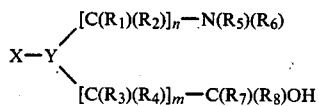

wherein
   X is a polymer backbone
   Y is a group derived from N,
   $R_1$, $R_2$, $R_3$ and $R_4$ are, independently, groups selected from H, a $C_1$–$C_4$ alkyl group and a halogen atom,
   $R_5$ and $R_6$ are, independently, groups selected from H, a $C_1$–$C_4$ alkyl group and a halogen atom, or together with the nitrogen atom form part of a heterocyclic ring containing 5 or 6 atoms with nitrogen being the only heteroatom,
   $R_7$ and $R_8$ are, independently, groups selected from H, a $C_1$–$C_4$ alkyl group, and a halogen atom, and each of n and m have a value from 0 to 10,
   such that the metal is complexed with the functionalised organic polymer through the nitrogen atom in the N($R_5$) ($R_6$) group and the oxygen atom in C($R_7$) ($R_8$)OH group.

2. A process as claimed in claim 1 characterised in that the hydroperoxide is an alkyl hydroperoxide.

3. A process as claimed in claim 1 characterised in that the olefin is ethylene and that an autocatalytic agent is added.

4. A process as claimed in claim 3 characterised in that the autocatalytic agent is ethylene oxide.

5. A process as claimed in claim 1 characterised in that the temperature of reaction is in the range 50°–150° C.

6. A process as claimed in claim 1 characterised in that the olefin to hydroperoxide molar ratio is in the range 2:1 to 20:1.

7. A process as claimed in claim 1 characterised in that the polymer bound organometallic complex comprises a metal selected from molybdenum and vanadium and a functionalised organic polymer of formula

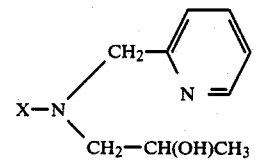

8. A process as claimed in claim 1, characterised in that the polymer is selected from the group consisting of polystyrene, a polyamide and a polyolefin.

9. A process as claimed in claim 8, characterised in that the polymer is polystyrene.

10. A process as claimed in claim 1 characterised in that the molar ratio of the organometallic complex to the hydroperoxide is between 0.005:1 and 0.1:1.

11. A process as claimed in claim 1 characterised in that between 1.2 and 50 volumes of the solvent are used per volume of the hydroperoxide.

12. A process as claimed in claim 1, characterised in that the olefin to hydroperoxide molar ratio is from 0.5:1 to 100:1.

* * * * *

UNITED STATES PATENT AND TRADEMARK OFFICE
CERTIFICATE OF CORRECTION

PATENT NO.   :   4,602,100

DATED        :   July 22, 1986

INVENTOR(S)  :   RAYMOND L. KELLY

It is certified that error appears in the above-identified patent and that said Letters Patent is hereby corrected as shown below:

Col. 2, line 33, "phenyl bis(salicylimide) should read --phenyl bis(salicylimine)--

Signed and Sealed this

Thirteenth Day of January, 1987

Attest:

DONALD J. QUIGG

Attesting Officer    Commissioner of Patents and Trademarks